(12) United States Patent
Lu

(10) Patent No.: US 8,454,496 B2
(45) Date of Patent: Jun. 4, 2013

(54) CAPSULE ENDOSCOPE WITH FLEXIBLE PRINTED CIRCUIT BOARD

(75) Inventor: Yiqun Lu, Hefie (CN)

(73) Assignee: Xiaoxun Zhu (CN)

( * ) Notice: Subject to any disclaimer, the term of this patent is extended or adjusted under 35 U.S.C. 154(b) by 994 days.

(21) Appl. No.: 10/598,694

(22) PCT Filed: Mar. 16, 2005

(86) PCT No.: PCT/CN2005/000317
§ 371 (c)(1),
(2), (4) Date: Sep. 8, 2006

(87) PCT Pub. No.: WO2005/087083
PCT Pub. Date: Sep. 22, 2005

(65) Prior Publication Data
US 2007/0142703 A1      Jun. 21, 2007

(51) Int. Cl.
*A61B 1/04*      (2006.01)
*A61B 1/06*      (2006.01)
(52) U.S. Cl.
USPC .................... 600/130; 600/109; 600/160
(58) Field of Classification Search
USPC .......................... 600/130, 109, 160
See application file for complete search history.

(56) References Cited

U.S. PATENT DOCUMENTS

| | | | | |
|---|---|---|---|---|
| 4,218,522 | A * | 8/1980 | Motoyoshi | 429/97 |
| 4,487,820 | A * | 12/1984 | Engelstein et al. | 429/100 |
| 7,195,588 | B2 * | 3/2007 | Homan et al. | 600/118 |
| 7,833,151 | B2 * | 11/2010 | Khait et al. | 600/109 |
| 2001/0051766 | A1 * | 12/2001 | Gazdzinski | 600/309 |
| 2002/0198439 | A1 * | 12/2002 | Mizuno | 600/109 |
| 2003/0020810 | A1 * | 1/2003 | Takizawa et al. | 348/68 |
| 2003/0171648 | A1 * | 9/2003 | Yokoi et al. | 600/109 |
| 2004/0171914 | A1 * | 9/2004 | Avni | 600/160 |
| 2004/0176685 | A1 * | 9/2004 | Takizawa et al. | 600/424 |
| 2005/0043634 | A1 * | 2/2005 | Yokoi et al. | 600/476 |
| 2006/0004255 | A1 * | 1/2006 | Iddan et al. | 600/160 |
| 2006/0004256 | A1 * | 1/2006 | Gilad et al. | 600/160 |
| 2006/0015013 | A1 * | 1/2006 | Gilad et al. | 600/160 |

FOREIGN PATENT DOCUMENTS

JP      2001-091860      *   6/2001

* cited by examiner

*Primary Examiner* — John P Leubecker
(74) *Attorney, Agent, or Firm* — Schmeiser, Olsen & Watts, LLP

(57) ABSTRACT

The present invention involves a new type of capsule pattern endoscope intended to greatly reduce the effective internal volume of the capsule pattern endoscope through reasonable structure arrangement. The technical proposal to implement the above invention is: a kind of capsule pattern endoscope comprises an intelligent capsule and an image-receiving device. The intelligent capsule includes a shell with an electronic circuit printed thereon, and an image information pick-up device including an image sensor and a lens optical system, an image signal processing and transmitting device, a light source, and a power supply, which are arranged inside the shell.

14 Claims, 3 Drawing Sheets

CAPSULE ENDOSCOPE WITH FLEXIBLE PRINTED CIRCUIT BOARD

FIELD OF THE INVENTION

The present invention relates to a device of endoscope. More specifically, the invention relates to a kind of capsule pattern endoscope.

BACKGROUND OF THE INVENTION

Generally, a miniature consists of two parts: intelligent capsule and image receiving device. Shaped like a pill capsule, the intelligent capsule is used for swallowing. It cannot only reach deep into the intestinal tracts inaccessible to traditional encoscopes, but also causes less pain to the patients when compared with traditional endoscopes. The intelligent capsule consists of the following parts: image information acquiring device, image signal transmitting device, light source, power source and outer shell, among which the image information acquiring device includes image sensor and lens optical system and the image signal transmitting device includes microwave transceiver and antenna. After entering the body, the intelligent is pushed to move inside the body by human muscle organization like foods to take pictures of interior of the body of parts where the capsule passes by along the way, which are sent out of human body digitally via the radio, received, stored and displayed by the image receiving device to complete examination of human body. Due to special use environment of these capsule pattern endoscopes, high requirements are imposed on its size and it is technically difficult to achieve small size and high performance using conventional electronic design and processing methods. In limited internal space, with smaller circuit boards and components, higher requirements are imposed on integration of the components, which is bound to result in increased technical complexity and difficulty in design and manufacturing. In addition, due to very large data quantity of the pictures taken, for instance, the data quantity of a 100000-pixel real-color image is about 200000 bytes (one byte includes 8 binaries), approximately 1.6 Mbit. When transmitting using 1 M-bit rate radio communication device, it takes about 2 seconds to finish transmitting a 100000-pixel real-color image. And presently, to complete one examination, it is necessary to take more than 20000 pictures, which will take a lot of communication time for sending the pictures taken and consume plenty of electricity during the communication process.

SUMMARY OF THE INVENTION

The present invention offers a new type of capsule pattern endoscope to overcome shortcomings of above existing technologies; through reasonable structure arrangement, the internal volume of the capsule is greatly reduced.

The technical proposal to realize the above invention is: a type of capsule pattern endoscope, including intelligent capsule and image receiving device; the intelligent capsule includes outer shell and image information acquiring device located inside the outer shell, image signal processing and transmitting device, light source, power source and the image information acquiring device includes image sensor and lens optical system and its characteristics is that there is PCB structure on the outer shell of the intelligent capsule.

The PCB structure may have one layer or multiple layers and may be provided with an additional bracket when necessary to support and fix the PCB structure.

Components or component set of the intelligent capsule are installed on the PCB or the bracket supporting the PCB. The components or component set include image information acquiring device, image signal transmitting device, light source and power source or certain components of the above devices, like controller dominated by CPU provided on the PCB, image processor, radio transreceiving signal processing chip or antenna component. The above devices may be separately or integrated provided.

The above components are integrated together with the outer shell, thus greatly reducing difficulty in manufacturing the system and meeting the systematic requirements of the system in a simple and practical manner.

The above PCB may be soft PCB and be provided with a bracket that can support the outer shell. After welding of the components or component set to the surface of the soft PCB, bend the PCB into the desired shape of outer shell.

Said PCB may be drum-type PCB with components or component set welded to the outer surface of the drum-type PCB and provided with protection layer externally.

In comparison with existing technologies, the beneficial effects of this invention are manifested in the following aspects:

1. The present invention, through use of larger surface area of the capsule pattern endoscope, greatly increases the internal available space, which means that more batteries can be carried or more functions can be provided.

2. The present invention uses outer shell to design and manufacture the circuit and its components so that the both requirements for integration of system components and technical complexity in designing and manufacturing are decreased, therefore making it easier to design and manufacture the device.

As a further improvement of the invention, an image compression processor is provided in said image signal processing device; a microwave transceiver that sends the compressed image data and controls image data is provided in the image signal-transmitting device.

The aforesaid image compression processor includes image compression device and image cutting device and may use any existing compression processing technologies.

The image compression processor in the outer shell may perform data compression of the pictures taken and use the microwave transmitter to transmit data of the compressed image to the external radio image receiving device, therefore greatly reducing power consumption during the data transmission process.

In this invention, the image-cutting device has the function of window cutting, capable of transmitting images of the entire window or transmitting images of small windows. For instance, the camera may take pictures of 1000*1000 pixels; through use of window cutting function of the image cutting device, only a small image of 200*200 pixels is taken from the image of 1000*1000 pixels and transmitted via radio under normal use conditions, whereas the entire image of 1000*1000 pixels is transmitted when performing examination of key areas. This can greatly reduce the data quantity of radio transmission and in the meanwhile ensure effects of examination of key areas.

The image compression processor also includes image compression rate adjusting device, which has the function of adjusting compression rate of original pictures taken, for instance, compression rate of compressing the data quantity of the image to ⅛ and 1/16 and others of the original image. The higher the compression rate of image compression, the smaller the data quantity of the image after compression; the lower the compression rate of image compression, the larger the data quantity of image after the compression and the lower the resolution of the image. Under normal use conditions, the image processor adjusts the image compression rate to 1/16 and transmits the image data after compression via radio; however, when performing examination of key areas, the image processor adjusts the image compression rate to 1/8 and transmits the image data after compression via radio. This can not only greatly reduce data quantity of radio transmission, but also ensure the effects of examination of key areas.

Devices in the image compression processor can be provided separately or integrated; for instance, an integrated chip may be used to perform all functions of the device.

Compared with existing technologies, the beneficial effects of this invention are manifested as follows: this invention may use various advanced compression technologies to greatly reduce data quantity of the images, increase the transfer rate of images and reduce power consumption during the communication process through image compression. Take the compression of static image for example, the data quantity of a 100,000 pixel real color image is approximately 200000 bytes (one byte includes 8 binaries), which can be compressed to 1/10 of the original image data, namely, approximately 20000 bytes by means of compressing the original image using JPEG2000. Again, take dynamic image compression for example; the data quantity may be reduced to 1/100 of its original value by means of compressing the image using MPEG4. Data quantity of the original image may also be greatly reduced by means of damage-free compression. Adequate utilization of various advanced compression technologies in designing of the new type of capsule pattern endoscope may overcome such shortcomings as low transfer rate of images and excessive power consumption encountered in existing similar systems.

As further improvements of this invention, the image receiving device may be provided with external controller and the intelligent capsule may be provided with corresponding controller; the external controller sends microwave control commands to the intelligent capsule and the controller intelligent endoscope completes certain special actions, such as control of image compression rate, image cutting, light source and lens optical system, etc.

The intelligent capsule is provided with a carrier capsule, which may have its valve, opened by the external controller so as to spray medicine to perform pathologic examination of the focus.

Unit members located inside the capsule cavity may be integrated system components as a whole or sub-part unit members may also be integrated.

Figure 1:
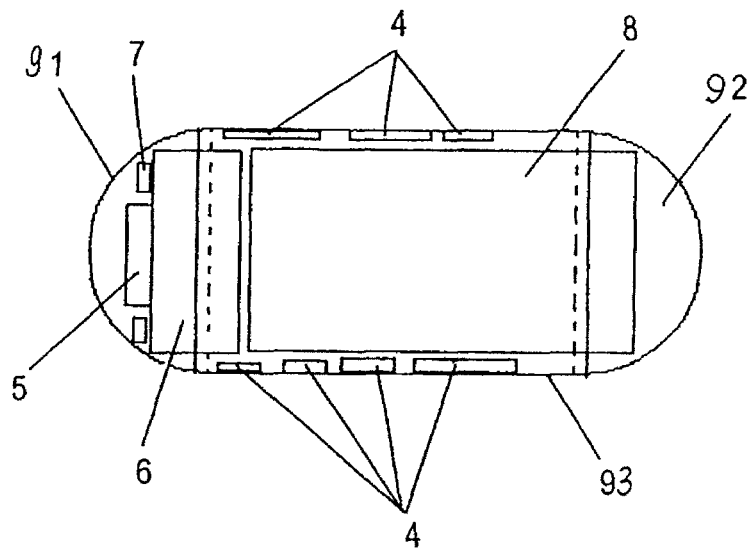
FIG. 1 is a schematic diagram illustrating example 1 and 2 embodying the invention concept.

Number in the figures: 1 intelligent capsule 2 image receiving device 3 soft PCB 4 component or component set 41 image compression processor 42 controller 43 microwave transceiver 5 lens 51 lens accessories 6 image sensor 7 lamp 8 internal capsule 9 outer shell 91 outer shell front cover 92 outer shell rear cover 93 Main body 10 power source 11 carrier capsule 12 photographing capsule 13 external image data processor 14 external controller 15 memory 16 display 17 computer interface 18 power device 19 external microwave transceiver

DESCRIPTION OF THE PREFERRED EMBODIMENTS

The invention will further be described with reference to the accompanying drawing:

Example 1

A device of capsule pattern endoscope including intelligent capsule 1 and image receiving device 2. Intelligent capsule 1 includes image information acquiring device, image signal transmitting device, light source, power source and outer shell, the image information acquiring device includes image sensor 6 and lens optical system 5 and 51, the intelligent capsule has soft PCB structure 3 on its outer shell 9 and has components or component set 4 welded on the PCB.

Figure 2:
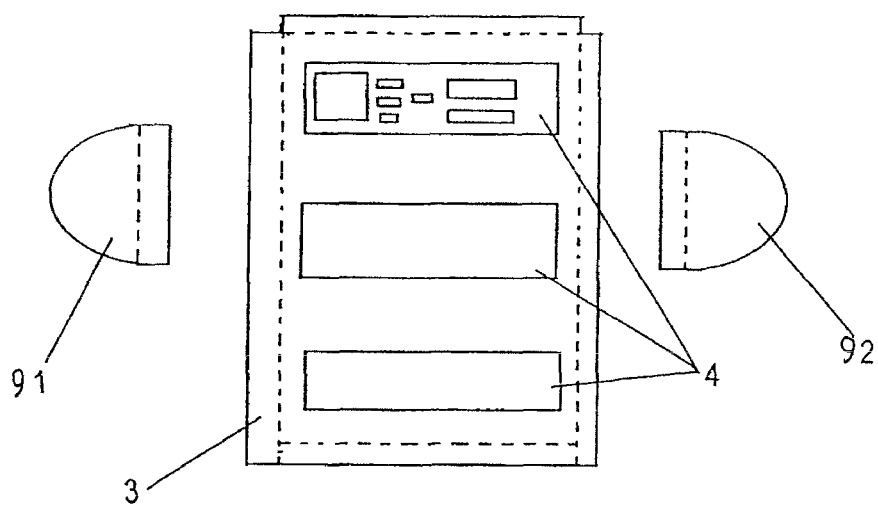
FIG. 2 is the structure schematic of PCB in example 1 and 2.

Refer to FIGS. 1 and 2. The outer shell includes body 93, front cover 91 and rear cover 92, which combine to form the capsule cavity, has PCB structure and components or component set 4 directly welded on the PCB. The components or component set 4 include controller 42 dominated by the CPU, image compression processor 41, microwave transceiving chip and antenna component 43.

As is shown in the figure, front cover 91 is made using accessories of the transparent objective lens of lens 5 and image sensor 6, lamp 7 are provided in corresponding positions in front cover 91.

Main body 93 and rear cover 92 may be separated from each other or integrated together. To achieve electromagnetic compatibility, it is possible to install the antenna component 43 on rear cover 92.

As is shown in figure, soft PCB 3 usually includes copper clad laminate, substrate and protective coating layer; required circuit etched on the copper clad layer using printing/etching technology is known as PCB in circuit board manufacturing technology, relevant components and component set 4 are directed welded on the outer or inner surface of the soft PCB 3, which can be rolled inward roughly into the drum or polygon column shape and installed on the bracket of the outer shell.

In this implementation example, design 13 mm diameter main body 93, 30 mm in length, weld the component or component set 4 onto the soft PCB 3 and attach them to the bracket of the outer shell; as long as the circuit uses component with an area of 37 mm×25 mm or component set 4 sized smaller than the area and the number of component or component set 4 does not exceed, it is possible to make sure that the soft PCB 3 can be rolled roughly into the drum shape. Under current technical conditions, the sizes of components necessary for the intelligent capsule 1 are: controller: 3 mm×3 mm×1 mm, microwave transceiving chip 43: 4 mm×4 mm×1 mm, image compression processor 41: 3 mm×4 mm×1 mm, components like resistor and capacitor: generally 1.5 mm×0.6 mm×0.5 mm. As long as the components are properly positioned, soft PCB 3 can be effectively rolled into main body 93 in the drum shape. The image sensor 6, sized approximately 8.5 mm×8 mm×6 mm, can be installed inside main body 93 and form the capsule pattern endoscope together with front cover 91 and rear cover 92.

Example 2

This implementation example is basically same as the above example except that main body of the outer shell is fabricated directly using column-shaped PCB.

The method is: use the technology of PCB in special or irregular shape; take capsule pattern endoscope 13 mm in design diameter and 30 mm in length, first mold press the PCB materials into 9 mm×9 mm×21 mm hollow polygon column, etch printed circuit on the surface of the hollow polygon column into PCB in special or irregular shape, install controller 42, image compression processor 41, microwave transreceiving chip and antenna component on the outer surface and cover with a 13 mm diameter round drum externally to as the protective layer to make main body 93, inside which lens 5, image sensor 6, lamp 7 are installed and place power source structure in internal capsule 8. Image sensor 6, lamp 7, outer shell main body 93, power source structure and other electronics structure connected together by means of lead wires to form the capsule pattern endoscope with front cover 91 and rear cover 92.

Example 3

Implementation example 3 differs from implementation example 1 in that image compression processor 41 is provided in the image information acquiring device and microwave transceiver 43 that sends compression image data and controls image data is provided in the image signal-transmitting device.

The intelligent capsule 1 in this implementation example takes the shape of capsule, lens 5, lens accessory 51 and lamp 7 as the lens system are installed at the front end cover 91 of the capsule, provided immediately adjacent lens 5 is image sensor 6, matching image sensor 6 is image compression processor 41, controller 42 and microwave transceiver 43 that sends compression image data and controls image data.

Figure 3:
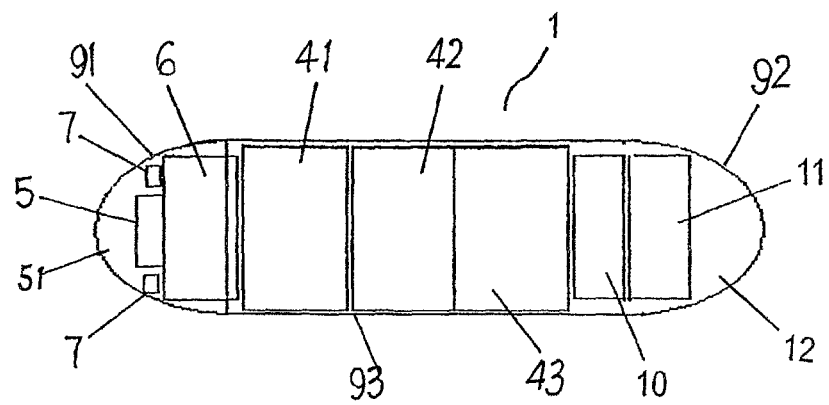
FIG. 3 is the structure schematic of intelligent capsule in example 3 and 4.

As is shown in FIG. 3, lens 5, image sensor 6 and lamp 7 are assembled together into the photographing device, inside which the components are combined together by means of welding, gluing or fastening.

The capsule cavity shall also contain power source 10 and carrier capsule 11. Among these, power source 10 can be realized through battery or power can be supplied by means of transmitting radio wave for remote power supply using antenna, that is, use large power radio transmitter to transmit radio wave, which is received by the antenna in the capsule pattern endoscope, for which the charge pump (diode) obtains induced charge to form current power supply or store the current into the capacitor or rechargeable battery, which will then supply power. The carrier capsule 11 is an enclosed box with controllable capsule door, which opens or closes under the action of the controller to complete sampling or chemical feeding.

In this implementation example, provided in the unit circuit of the capsule cavity are image compression processor 41, controller 42 and microwave transmitter that sends compression image data and controls data, among which image compression processor 41 may perform damaging or damage-free compression of the images by means of hardware or compression software and the microwave transceiver 43 that sends compression image data and controls data is composed of microwave transceiving chip and supplementary antenna.

The capsule pattern endoscope that can work is formed by connecting the aforesaid photographing component, image compression processor 41, controller 42, microwave transceiver 43 and power source 10 together, installing said components and carrier capsule 11 into the photographing capsule 12 and then connecting lens accessory 51 of the lens 5 with the front part of the photographing capsule 12. In this implementation example, lens 5, image sensor 6, image compression processor 41 are enclosed and integrated together into a component, for instance, ADCM-2650 component.

Figure 4:
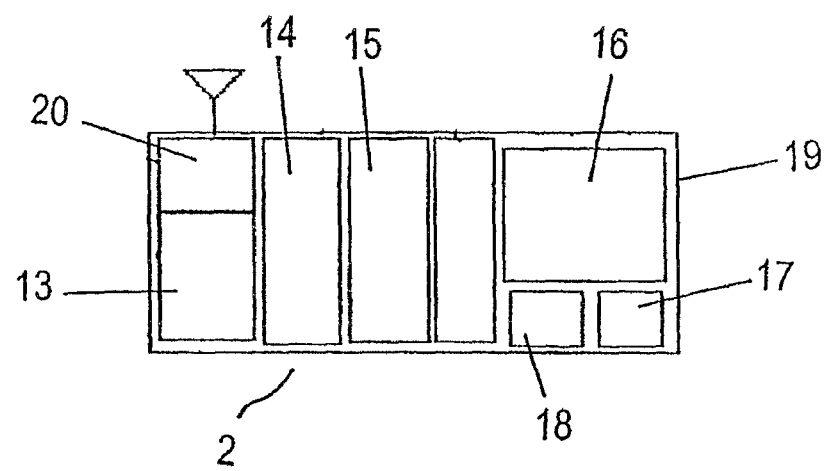
FIG. 4 is the structure schematic of image receiving device in example 3 and 4.

In this implementation example, the supplementary image-receiving device is shown in FIG. 4. Image receiving device 2 includes microwave transceiver 43 that receives compression data and control signal transmitted by the microwave, image data processor 13, external controller 14, memory 15, display 16, computer interface 17 and power device 18; the unit circuits are provided inside the external shell 9 and connected with each other by means of lead wires.

Power source structure 10 in capsule pattern endoscope intelligent capsule 1 supplies power to the components via lead wires. Controller 42 is connected with the components by means of lead wires to send control commands to the components. Under the control of controller 42, image sensor 6 takes pictures via objective lens accessory 51 and lens 5 under the light of lamp 7, image data are outputted to the image compression processor 41 via the lead wire for image compression, the compressed image data are outputted to microwave transceiver 43 of the compression image data and control data via lead wires for transmitting out of human body and image receiving device 2 receives, stores, decompresses and displays the compression image data to complete examination of interior of human body. Also, the external image receiving device 2 may send microwave control commands via intelligent capsule 1 to controller 42, requesting the capsule pattern endoscope to complete certain special actions, for instance, to stop or start photographing, etc.

Figure 5:
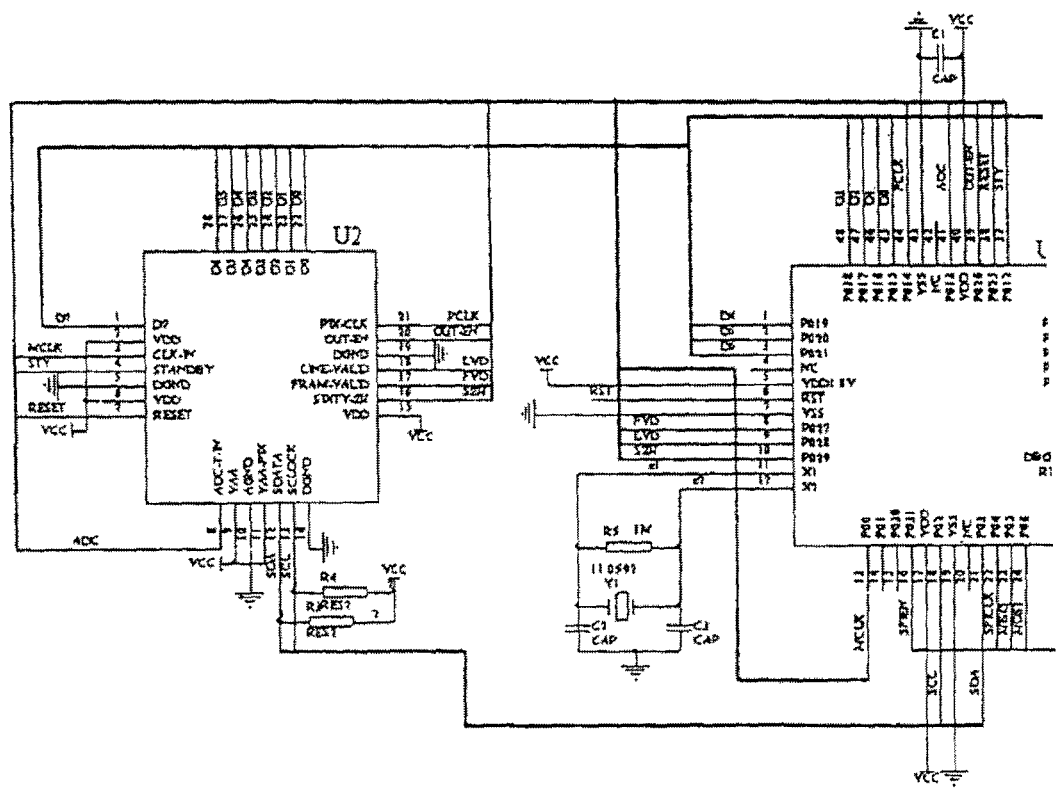
FIG. 5 shows the circuit schematic of image compression processor in example 3 and 4.

As is shown in FIG. 5, image sensor U2 uses low power consumption CMOS sensor, for instance, type MI-SOC-0133 or T5740. Image compression compressor U1 includes image compression device, image processing device, image cutting device and image compression rate adjusting device. Image compression processor U1 uses high speed micro power consumption CPU processor, for instance, ARM processor to realize functions of the above devices via software or may use ASIC hardware or DSP chip to realize functions of the device via software.

Image compression device performs image compression inside image compression processor U1, which performs compression computation of image data stored in its internal RAM under the control of programs and stores the compressed image data into the internal RAM.

Image processing device, under the control of programs, image compression processor U1 generates various time sequences and control commands required by image sensor U2, which are sent to corresponding pins of U1 via I/O pin so that U2 may operate in the specified manner and outputs image format time sequence via data output time sequence control line of U2 as well as image data via the data output line of U2. In the meanwhile, image compression processor U1 receives image format time sequence outputted by data output time sequence control line of image sensor U2, receives image data outputted by data output line of image sensor U2 under the control of the time sequence and stores the data stream into the RAM inside image compression processor U1 to complete acquiring the image data.

Image cutting device is provided in image sensor U2. When it is necessary to perform the cutting operation, the controller 42 (the controller may be image compression processor U1) writes cutting data into the cutting register in image sensor U2 via the lead wires connecting image sensor U2 and the controller 42, which works together with a data comparer to compare image data and give the image data after cutting. For instance, the picture taken by image sensor 6 is 1000(row)*1000(column) pixel original image. When it is necessary to cut the image, for instance, it is possible to write cutting data 200 into the 'row' comparison register of the cutting register and cutting data 300 into the 'column' register of the cutting register. Then, each pixel data of image taken by U2 is compared with cutting data stored in 'row', 'column' registers of the cutting register via the data comparer; when the row data of the pixel in the image is greater than 200 or the column data is greater than 300, the pixel is abandoned; when the row data of pixel in the image is greater, only small image of 200 (row)*300 (column) pixels remains in the image when such handling of the entire image is completed, therefore, completing cutting of the image. In addition, the image-cutting device may be provided in the controller and the action process is the same as mentioned above.

Image compression rate adjusting device: the device is provided in image compression processor U1. When it is necessary to adjust image compression rate, the controller 42 (the controller may be image compression processor U1) writes new compression rate data into the compression magnitude control register in image compression processor U1 via the lead wire connecting the image compression processor U1 and the controller 42. For instance, if the original compression magnitude data is 8, the compression circuit inside the image compression processor compresses the data quantity of the image to approximately ⅛ of the data quantity of the original image according to compression magnitude data 8. And, when it is necessary to make adjustments of image compression rate, write new compression rate data 16 into the compression magnitude control register and the compression circuit inside the image compression processor will, according to compression magnitude data 16, compresses the data quantity of the image to approximately 1/16 of the data quantity of the original image, therefore achieving adjustment of the compression rate.

Image transmitting device: U1 is connected to the pin corresponding to JP1 via the pin corresponding to the series equipment interface and controls JP1 to send out the compressed image data stored in the RAM inside U1 via radio.

Microwave transceiver JP1 that transmits compression image data and controls image data uses micro power consumption microwave communication chip, for instance, ANTENNA. Standard connection method is sampled among U1, U2 and JP1.

Operating process of the system:
1. The image sensor receives control commands via the series interface, U1 controls data line SDA via I/O pin, and clock line SCL sends commands to the interface to set the operating mode of U2.
2. U1 outputs control time sequence under the control of software and control and time sequence signal to the control line via I/O pin, which includes control line ADC, control line RESET, control line STY, synchronization time sequence input control line MCLK, via which I/O pin of U1 outputs control time sequence to enable U2 to operate.
3. After U2 starts to operate, U1 controls U2 data output enabling control line OUT-EN via I/O pin to output image data to data line.
4. U2 outputs 'format time sequence of image signal' via data output time sequence control line, pixel time sequence line PCLK, row time sequence line LVD, frame time sequence line FVD, and field time sequence line SZH.
5. U1 receives 'format time sequence of image signal' from I/O pin via corresponding time sequence control line and image data outputted by U2 via data line DO-07 under the control of format time sequence and stores the data into register RAM inside U1.
6. After U1 receives data of a complete image according to format time sequence outputted by U2, U1 controls U2 via control line STY so that U2 stops working temporarily.
7. U1 shifts to cutting and compression handling program under the control of program; for image data stored in the internal RAM, the compression processor performs operations in accordance with data currently written into the image cutting register and image compression rate register, for instance, perform cutting operation on the image according to data in the cutting register, carry out compression computation according to data in the image compression rate register and then stores the treated image data into the internal RAM to complete cutting and compression of the image.
8. U1 controls JP1 to start to work via control line SPISEN of the series equipment and transmits the data of the compressed image to JP1 via its main output line MOSI, main input line MISO and main clock line SPICLK, which will then send out the image data via radio to complete the work.
9. Handle the next image under the control of U1.
10. The system operates continuous in the aforesaid mode.

Example 4

In this implementation example, the setting of the capsule outer shell is identical to that of implementation example 2 and the internal setting is identical to that of implementation example 3.

What is claimed is:
1. A capsule pattern endoscope comprising:
   an intelligent capsule comprising:
      a flexible PCB structure;
      an outer shell having a front cover, a rear cover, and a main body, wherein the main body consists essentially of the flexible PCB structure;
      shell;
      an image information acquiring device operatively positioned relative to the main body and comprising:
         an image sensor, operatively positioned on the flexible PCB structure within the outer shell; and
         a lens optical system, operatively positioned on the flexible PCB structure within the outer shell and operatively connected to the image sensor;
      an image signal processing and transmitting device operatively positioned on the flexible PCB structure within the outer shell;
      a light source, operatively positioned on the flexible PCB structure within the outer shell; and
      a power source, operatively positioned within the outer shell and operatively connected to the flexible PCB structure and physically separate and spaced physically apart from the flexible PCB structure; and
   an image receiving device operatively positioned relative to the intelligent capsule.
2. The capsule pattern endoscope of claim 1, wherein the image signal processing and transmitting device further comprises:
   antenna structure operatively positioned proximate the rear cover of the outer shell.
3. The capsule pattern endoscope of claim 1 wherein the image information acquiring device further comprises:
   an image compression processor.
4. The capsule pattern endoscope of claim 3 wherein the image compression processor includes an image-cutting device.

5. The capsule pattern endoscope of claim 3, wherein the image compression processor includes an image compression rate adjusting device.

6. The capsule pattern endoscope of claim 3, wherein the image compression processor comprises a CPU, DSP or ASIC processor.

7. The capsule pattern endoscope of claim 1, wherein the image signal processing and transmitting device further comprises:
   a microwave transceiver capable of sending compressed image data.

8. The capsule pattern endoscope of claim 1, wherein the image sensor comprises:
   a CMOS image sensor.

9. The capsule pattern endoscope of claim 1 further comprising:
   a microwave communication chip.

10. The capsule pattern endoscope of claim 1, wherein the image-receiving device includes an external controller compatible with a corresponding controller of the intelligent capsule.

11. The capsule pattern endoscope of claim 10, wherein the external controller is capable of sending microwave control commands to the intelligent capsule so that the controller of the intelligent capsule completes the commands received from the external controller.

12. The capsule pattern endoscope of claim 1, wherein the flexible PCB structure comprises a cylindrical shape.

13. The capsule pattern endoscope of claim 12, wherein the cylindrical shaped flexible PCB structure is operatively connected to the power source.

14. The capsule pattern endoscope of claim 13, wherein the cylindrical shaped flexible PCB structure us and the power source are operatively positioned inside the outer shell.

* * * * *